United States Patent
Nielsen et al.

(10) Patent No.: US 10,844,405 B2
(45) Date of Patent: *Nov. 24, 2020

(54) ENZYMES AND MICROORGANISMS FOR THE PRODUCTION OF 1,3-BUTADIENE AND OTHER DIENES

(71) Applicant: Arizona Board of Regents on Behalf of Arizona State University, Scottsdale, AZ (US)

(72) Inventors: David Nielsen, Tempe, AZ (US); Shawn Pugh, Mesa, AZ (US); Rebekah McKenna, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,377

(22) Filed: Nov. 8, 2018

(65) Prior Publication Data

US 2019/0194695 A1  Jun. 27, 2019

Related U.S. Application Data

(63) Continuation of application No. 15/022,540, filed as application No. PCT/US2014/050854 on Aug. 13, 2014, now Pat. No. 10,125,377.

(60) Provisional application No. 61/879,543, filed on Sep. 18, 2013.

(51) Int. Cl.
*C12P 5/02* (2006.01)
*C12N 9/88* (2006.01)

(52) U.S. Cl.
CPC .............. *C12P 5/026* (2013.01); *C12N 9/88* (2013.01); *C12Y 401/01* (2013.01); *Y02E 50/30* (2013.01)

(58) Field of Classification Search
None
See application file for complete search history.

(56) References Cited

U.S. PATENT DOCUMENTS

| 7,079,863 | B2 | 7/2006 | Chikaishi |
| 9,150,884 | B2 | 10/2015 | Nielsen et al. |
| 9,944,955 | B1 | 4/2018 | Wang et al. |
| 10,125,377 | B2 * | 11/2018 | Nielsen ................ C12N 9/88 |
| 10,174,346 | B2 | 1/2019 | Nielsen et al. |
| 2002/0127299 | A1 | 9/2002 | Ago |
| 2012/0021478 | A1 | 1/2012 | Osterhout |

FOREIGN PATENT DOCUMENTS

| WO | 2012122333 A1 | 9/2012 |
| WO | 2013130426 | 9/2013 |
| WO | 2013172928 A1 | 11/2013 |
| WO | 2015031048 A1 | 3/2015 |
| WO | 2015041776 A1 | 3/2015 |
| WO | 2019018302 A1 | 1/2019 |
| WO | 2019023019 A1 | 1/2019 |

OTHER PUBLICATIONS

U.S. Appl. No. 16/631,232, filed Jan. 15, 2020, Nielsen et al.
U.S. Appl. No. 16/633,525, filed Jan. 23, 2020, Nielsen et al.
Bhuiya, M. W., et al. "Structure and mechanism of ferulic acid decarboxylase (FDC1) from *Saccharomyces cerevisiae*." Appl. Environ. Microbiol. 81.12 (2015): 4216-4223.
Kisselev, L.. "Polypeptide release factors in prokaryotes and eukaryotes: same function, different structure." Structure, 2002, vol. 10: 8-9.
Whisstock, J. C., et al. "Prediction of protein function from protein sequence and structure." Quarterly reviews of biophysics 36.3 (2003): 307-340.
Witkowski, A., et al. "Conversion of a ß-ketoacyl synthase to a malonyl decarboxylase by replacement of the active-site cysteine with glutamine." Biochemistry 38.36 (1999): 11643-11650.
International Searching Authority, International Search Report and Written Opinion for application PCT/US2014/050854, dated Feb. 6, 2015.

* cited by examiner

*Primary Examiner* — Iqbal H Chowdhury
(74) *Attorney, Agent, or Firm* — Quarles & Brady LLP

(57) ABSTRACT

A method for the in vivo production of 1,3-butadiene from 2,4-pentadienoate is described (FIG. 1). Enzymes capable of decarboxylating 2,4-pentadienoate to 1,3-butadiene have been discovered. Recombinant expression of these newly discovered enzymes has resulted in the engineering of microorganisms capable of producing 1,3-butadiene when cultured in the presence of 2,4-pentadienoate. 1,3-butadienoate is an important monomer used in the manufacturing of rubbers and plastics. This invention will help to enable the biological production of 1,3-butadiene from renewable resources such as sugar, for example.

9 Claims, 4 Drawing Sheets
Specification includes a Sequence Listing.

ENZYMES AND MICROORGANISMS FOR THE PRODUCTION OF 1,3-BUTADIENE AND OTHER DIENES

CROSS-REFERENCE TO RELATED APPLICATIONS

This application is a continuation of U.S. patent application Ser. No. 15/022,540, filed on Mar. 16, 2016, which is a National Stage Entry of International Application No. PCT/US2014/050854, filed Aug. 13, 2014, which claimed the benefit of U.S. Provisional Patent Application No. 61/879,543, filed on Sep. 18, 2013, the disclosures of which are incorporated by reference herein in their entirety.

BACKGROUND OF THE INVENTION 1,3-Butadiene is a useful and versatile chemical used for the production of numerous fine and commodity chemicals. Major products of note include butadiene rubber and poly(styrene-co-butadiene). 1,3-Butadiene is typically derived from petrochemical feedstocks including ethylene and as such its market price is tightly correlated with that of crude oil and natural gas and, perhaps more importantly, it is non-renewable. A sustainable alternative to conventional 1,3-butadiene production, involves the engineering of microorganisms with the novel ability to synthesize it at high levels and directly from renewable resources.

However, at present an inexpensive and sustainable source of 1,3-butadiene remains undeveloped. This is in part due to the fact that one of the key pathway enzymes has yet to be discovered or engineered. More specifically, there are at present no natural or engineered enzymes known to display 2,4-pentadienoate decarboxylase activity.

In light of the foregoing, it is an advancement in the current state of the art to provide a method by which 2,4-pentadienoate can be enzymatically decarboxylated to form 1,3-butadiene. This conversion is exceptionally advantageous if it is achieved within a single host cell that produces 2,4-pentadienoate directly from a renewable substrate such as glucose. Moreover, it is additionally advantageous if said method is generalizable, in that it is further amenable for use with other organic acid substrates possessing 2,4-dienoate functionality.

SUMMARY OF THE INVENTION

The embodiments described herein relate to a methods for the production of 1,3-butadiene from a recombinant cell.

In one aspect, certain embodiments relate to methods that include culturing a recombinant host cell with 2,4-pentadienoate, the recombinant host cell expressing at least one gene encoding at least one polypeptide configured for 2,4-pentadienoate activity, wherein expression in the recombinant host cell of the at least one gene encoding at least one polypeptide configured for 2,4-pentadienoate activity provides increased production of 1,3-butadiene in the recombinant host cell relative to a control recombinant host cell lacking expression of the at least one gene encoding the at least one polypeptide configured for 2,4-pentadienoate activity.

In another aspect, certain embodiments relate to methods for the production of 1,3-butadiene from a recombinant cell that include:
(i) contacting a recombinant host cell with at least one carbon source, the recombinant host cell including the ability to:
over produce 2,4-pentadienoate; and
express at least one gene encoding at least one polypeptide having 2,4-pentadienoate decarboxylase activity; and
(ii) culturing said recombinant cell under conditions sufficient to produce 1,3-butadiene, wherein expression of the at least one gene encoding at least one polypeptide having 2,4-pentadienoate decarboxylase activity provides increased production of 1,3-butadiene in the recombinant host cell relative to a control recombinant host cell lacking expression of the at least one gene encoding the at least one polypeptide having 2,4-pentadienoate decarboxylase activity.

These and other aspects of the invention will be apparent upon reference to the following detailed description and figures. To that end, any patent and other documents cited herein are hereby incorporated by reference in their entirety.

BRIEF DESCRIPTION OF THE TABLES

Table 1 compares the difference in 1,3-butadiene concentration as measured by FIS in the headspace over resting cell cultures of *E. coli* BW25113(DE3) pTrc99A and *E. coli* BW25113(DE3) pTrc99A-FDC1 when incubated in PBS buffer supplemented with trans-2,4-pentadienoate.

TABLE 1

| | 1,3-butadiene (µg/ml gas) | |
| --- | --- | --- |
| Strain | 3 h | 24 h |
| Bl21(de3) ptrc99a | 0.088 ± 0.008 | 0.058 ± 0.001 |
| Bl21(de3) ptrc99a-fdc1 | 3.00 ± 0.62 | 8.94 ± 2.56 |

Table 2 compares the difference in 1,3-butadiene concentration as measured by FIS in the headspace over resting cell cultures of *E. coli* BW25113(DE3) pTrc99A and *E. coli* BW25113(DE3) pTrc99A-FDC1 when grown in LB broth supplemented with trans-2,4-pentadienoate.

TABLE 2

| | 1,3-butadiene (µg/ml gas) | |
| --- | --- | --- |
| Strain | 3 h | 24 h |
| Bl21(de3) ptrc99a | 0.017 ± 0.003 | 0.053 ± 0.015 |
| Bl21(de3) ptrc99a-fdc1 | 0.053 ± 0.015 | 0.462 ± 0.103 |

Table 3 compares the difference in 1,3-butadiene concentration as measured by FIS in the headspace over resting cell cultures of E. coli BW25113(DE3) pTrc99A and E. coli BW25113(DE3) pTrc99A-FDC1 when incubated in PBS buffer supplemented with cis-2,4-pentadienoate.

TABLE 3

| Strain | 1,3-butadiene ($\mu$g/ml gas) | |
| --- | --- | --- |
|  | 3 h | 24 h |
| Bl21(de3) ptrc99a | 0.193 ± 0.023 | 0.194 ± 0.024 |
| Bl21(de3) ptrc99a-fdc1 | 0.347 ± 0.065 | 0.475 ± 0.003 |

DETAILED DESCRIPTION OF THE INVENTION

Embodiments described herein relate to a methods and nucleic acids for the in vivo production of 1,3-butadiene from 2,4-pentadienoate.

1,3-Butadiene is an important monomer used in the manufacturing of rubbers and plastics. This invention will help to enable the biological production of 1,3-butadiene from renewable resources such as sugar, for example.

Figure 1:
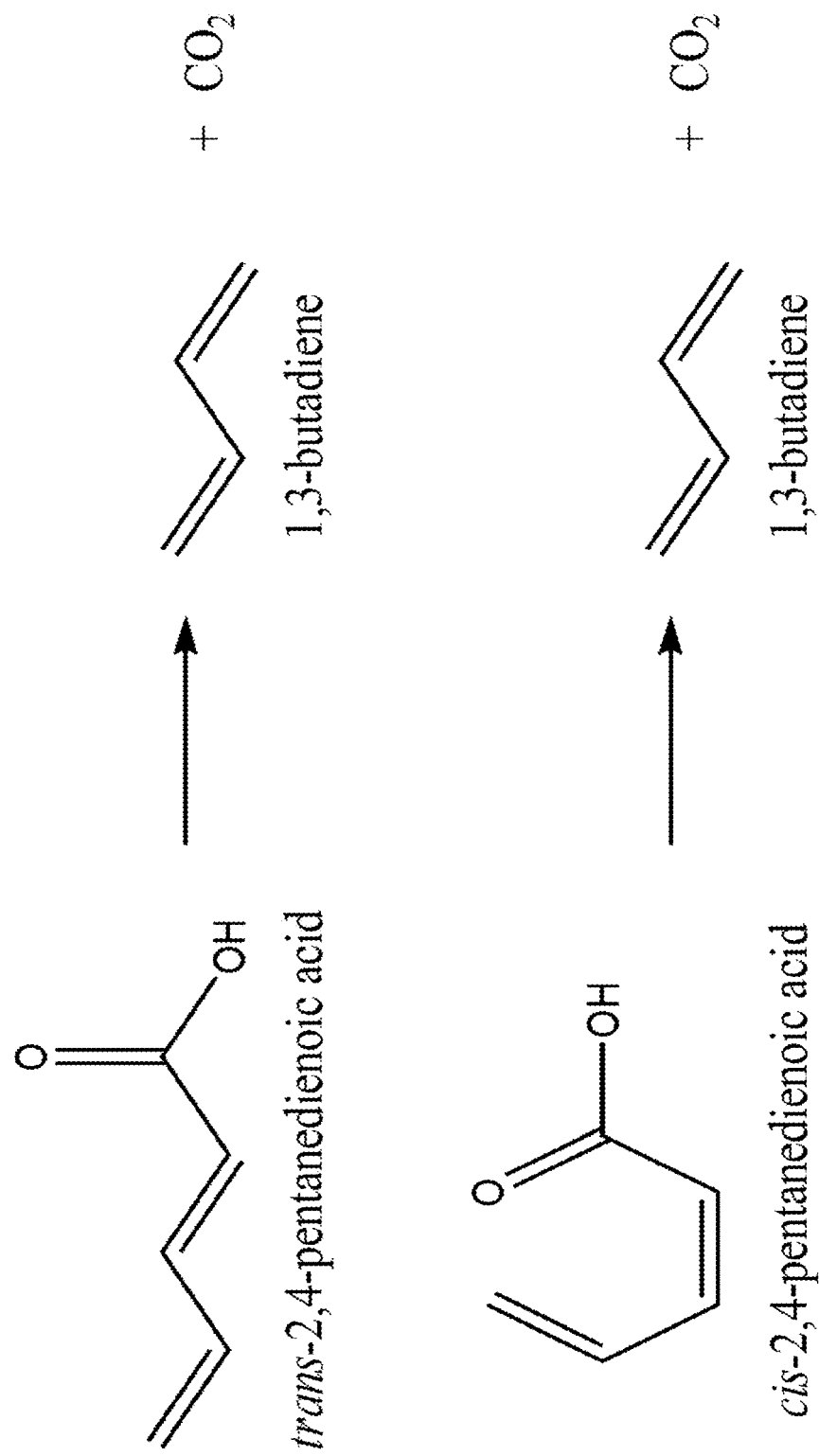
FIG. 1 illustrates a conversion of trans- and cis-2,4-pentadienoate to 1,3-butadiene via 2,4-pentadienoate decarboxylase, according to embodiments of the invention.

Embodiments described herein comprise the discovery of novel enzymes capable of producing 1,3-butadiene via the decarboxylation of 2,4-pentadienoate (as shown in FIG. 1). In addition, materials and methods are described for the engineering of novel microorganisms capable of producing 1,3-butadiene when cultured in the presence of 2,4-pentadienoate. To date, enzymes or organisms capable of performing this reaction have not been identified or described. This enzymatic reaction is of great interest to several companies focused on the development of microorganisms capable of producing 1,3-butadiene directly from renewable substrates such as sugars as it is an essential step in the larger pathway. As such, our discovery will be an essential element to the success of those efforts.

The following abbreviations and definitions will be used for the interpretation and specification of the claims.

As used herein, the terms "2,4-pentadienoate", "cis-2,4-pentadienoate", "trans-2,4-pentadienoate", "pentadienoate", "2,4-pentadienoic acid", "cis-2,4-pentadienoic acid", "trans-2,4-pentadienoic acid", and "pentadienoic acid" are used interchangeably, except the cis and trans isomers refer to their respective structures.

As used herein, the terms "1,3-butadiene" and "butadiene" are used interchangeably.

As used herein, the terms "2,4-pentadienoate decarboxylase", "cis-2,4-pentadienoate decarboxylase", "trans-2,4-pentadienoate decarboxylase", "pentadienoate decarboxylase", "2,4-pentadienoic acid decarboxylase", "cis-2,4-pentadienoic acid decarboxylase", "trans-2,4-pentadienoic acid decarboxylase", and "pentadienoic acid decarboxylase" are used interchangeably, except the cis and trans isomers refer to their respective structures.

The term "2,4-pentadienoate decarboxylase activity" refers to the ability of a protein to catalyze the direct conversion of 2,4-pentadienoate to 1,3-butadiene.

The term "fermentable carbon substrate" refers to a carbon source capable of being metabolized by the host organisms of embodiments described herein and particularly carbon sources selected from the group consisting of monosaccharides, oligosaccharides, polysaccharides, organic acids, glycerol, and one-carbon substrates or mixtures thereof.

The term "host" refers to a suitable cell line such as a strain of bacteria, for example, into which genes can be transferred to impart desired genetic attributes and functions.

The term "$OD_{600}$" refers to the measurement of optical density at 600 nm, a standard metric of cell growth used by those familiar in the art.

The term "gene" refers to a nucleic acid fragment that expresses a specific protein, including regulatory sequences preceding (5' non-coding sequences) and following (3' non-coding sequences) and the coding sequence. "Native gene" or "wild type gene" refers to a gene as found in nature with its own regulatory sequences. "Endogenous gene" refers to a native gene in its natural location in the genome of an organism. "Foreign gene" refers to a gene not normally found in the host organism but that is introduced into the host organism by gene transfer. Foreign genes can comprise native genes inserted into a non-native organism, or chimeric genes.

The term "expression", as used herein, refers to the transcription and stable accumulation of sense (mRNA) or antisense RNA derived from the nucleic acid fragment used in embodiments described herein. Expression may also refer to the translation of the mRNA into a polypeptide. "Overexpression" refers to the production of a gene product in a transgenic organism that exceeds levels of production in the wild-type host or native organisms.

"RNA transcript" refers to the product resulting from RNA polymerase-catalyzed transcription of gene or other a DNA sequence. "Messenger RNA (mRNA)" refers to the RNA that is without introns and can be translated into a protein by the cell. "cDNA" refers to double-stranded DNA that is complimentary to and derived from mRNA. "Sense" RNA refers to RNA transcript that includes the mRNA and so can be translated into protein by the cell.

"Transformation" refers to the transfer of a nucleic acid fragment into the genome of the host organism, resulting in genetically-stable inheritance. Host organisms containing the transformed nucleic acid fragments are referred to as "transgenic" or "recombinant" or "transformed" organisms.

The terms "plasmid" and "vector" refer to an extra chromosomal genetic element often carrying genes which are not part of host native genome nor the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The present disclosure describes the discovery of genes encoding polypeptides displaying 2,4-pentadienoate decarboxylase activity. That is, enzymes with the novel ability to decarboxylate 2,4-pentadienoate to 1,3-butadine (as shown in FIG. 1). This invention also comprises an in vivo method for the production of 1,3-butadiene via a recombinant host cell expressing at least one gene encoding a polypeptide having 2,4-pentadienoate decarboxylase activity to convert 2,4-pentadienoate to 1,3-butadiene.

While this invention provides a biological route for the conversion of 2,4-pentadienoate to 1,3-butadiene, it further supports the production of 1,3-butadiene directly from renewable substrates such as glucose. 1,3-Butadiene is useful, for example, for the synthesis of numerous chemical and polymer products. Accordingly, the present invention provides a method for the production of 1,3-butadiene comprising: i) contacting a recombinant host cell with 2,4-pentadienoate, where said recombinant host: a) expresses at least one gene encoding a polypeptide 2,4-pentadienoate decarboxylase activity; and ii) growing said recombinant cell for a time sufficient to produce 1,3-butadiene. The present invention also provides a method for the production of 1,3-butadiene comprising: i) contacting a recombinant host cell with a fermentable carbon source, where said recombinant host: a) has been engineered to endogenously synthesize 2,4-pentadienoate from fermentable substrates; and b) expresses at least one gene encoding a polypeptide 2,4-pentadienoate decarboxylase activity; and ii) growing said recombinant cell for a time sufficient to produce 1,3-butadiene. Additionally, the invention provides a recombinant host cell comprising: a) at least one gene encoding a polypeptide having 2,4-pentadienoate decarboxylase activity.

Genes

The key enzymatic activities used in the present disclosure are encoded by a number of genes. The principal enzyme activity includes 2,4-pentadienoate decarboxylase. These activities may also be displayed by enzymes whose principal natural substrates are not 2,4-pentadienoate, but also those which have the natural capacity to utilize these substrates or which can be engineered to display these activities. Thus, it will be appreciated that the present invention is not limited to the genes encoding polypeptides having the specific activities mentioned herein, but will encompass any suitable homologs of such genes that may be obtained by standard methods. Methods of obtaining homologs to these genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR)). For example, genes encoding homologs of the polypeptides that alone or in combination have the above mentioned activity could be isolated directly by using all or a portion of the known sequences as DNA hybridization probes to screen libraries from any desired plant, fungi, yeast, or bacteria using methodology well known to those skilled in the art. Specific oligonucleotide probes based upon the desired nucleic acid sequences can be designed and synthesized by methods known in the art. Moreover, the entire sequences can be used directly to synthesize DNA probes by methods known to those skilled in the art, such as random primers DNA labeling, nick translation, or end-labeling techniques or RNA probes using available in vitro transcription systems. In addition, specific primers can be designed and used to amplify a part of or full length of the instant sequences. The resulting amplification products can be labeled directly during amplification reactions or labeled after amplification reactions, and used as probes to isolate full-length cDNA or genomic fragments under conditions of appropriate stringency.

Microbial Production Hosts

The host organism of the present disclosure will include any organism capable of expressing the genes encoding a polypeptide that displays 2,4-pentadienoate decarboxylase activity. Typically, the production organism will be restricted to microorganisms or plants. Microorganisms useful in the present invention include, but are not limited to enteric bacteria (*Escherichia* and *Salmonella*, for example) as well as *Bacillus, Acinetobacter, Actinomycetes* such as *Streptomyces, Corynebacterium, Cupriavidus, Acetogens* such as *Clostridium, Methanotrophs* such as *Methylosinus, Methylomonas, Rhodococcus* and *Pseudomonas; Cyanobacteria,* such as *Rhodobacter* and *Synechocystis*; yeasts, such as *Saccharomyces, Zygosaccharomyces, Kluyveromyces, Candida, Hansenula, Debaryomyces, Mucor, Pichia,* and *Torulopsis*; and filamentous fungi such as *Aspergillus, Fusarium, Penicillium,* and *Arthrobotrys,* and algae, for example. Co-expressing at least one gene encoding a polypeptide having 2,4-pentadienoate decarboxylase activity can result in the production of large quantities of 1,3-butadiene.

The method of production defined in this invention involves the discovery and incorporation of genes encoding polypeptides displaying 2,4-pentadienoate decarboxylase activity into a single host organism and the use of those organisms to convert 2,4-pentadienoate to 1,3-butadiene. The 2,4-pentadienoate can be supplied exogenously or synthesized endogenously by the host organism. This invention relies upon the novel identification of genes encoding 2,4-pentadienoate activity and, preferably, those genes which when expressed in a recombinant host organism can display such activities. Novel genes encoding 2,4-pentadienoate activity were discovered by evaluating the activity of numerous putative candidates in recombinant hosts. Each gene was amplified from genomic or clonal DNA samples via PCR, cloned into an appropriate expression vector, and transformed into *E. coli*. Screening assays were then performed on both whole cells and cell extracts. 2,4-Pentadienoate decarboxylase activity was investigated via the conversion of exogenous 2,4-pentadienoate to 1,3-butadiene.

EXAMPLES

The present invention is further defined in the following Examples. It should be understood that these Examples, while indicating preferred embodiments of the invention, are given by way of illustration only. From the above discussion and these following Examples, one skilled in the art can ascertain the essential characteristics of this invention, and without departing from the spirit and scope thereof, can make various changes and modifications of the invention to adapt it to various uses and conditions.

Procedures required for PCR amplification, DNA modifications by endo- and exonucleases for generating desired ends for cloning of DNA, ligation, and bacterial transformation are well known in the art. The standard molecular biology techniques used herein are well-known in the art and described by Sambook, J., Fritsch, E. F., and Maniatis, T., Molecular Cloning: A Laboratory Manual, 2nd ed.; Cold Spring Harbor Laboratory: Cold Spring Harbor, N.Y., 1989.

Materials and methods suitable for the maintenance and growth of microbial cultures are well known in the art. Methods and techniques suitable for use in the following set of Examples may be found for example, as described in Manual of Methods for General Bacteriology; Gerhardt, P., Murray, R. G. E., Costilow, R. N., Nester, E. W., Wood, W. A., Krieg, N. R., and Phillips, G. B., Eds., American Society for Microbiology: Washington, D.C., 1994. All reagents used in the Examples were purchased from Sigma Aldrich (St. Louis, Mo.). Restriction enzymes, polymerases, and ligase were purchased from New England Biolabs (Ipswich, Mass.). Nutrients and chemicals used for the growth and maintenance of cells were purchased from DIFCO Laboratories (Detroit, Mich.).

Cloning of Candidate Genes Encoding 2,4-Pentadienoate Decarboxylase Activity from *S. cerevisiae*

Figure 2:
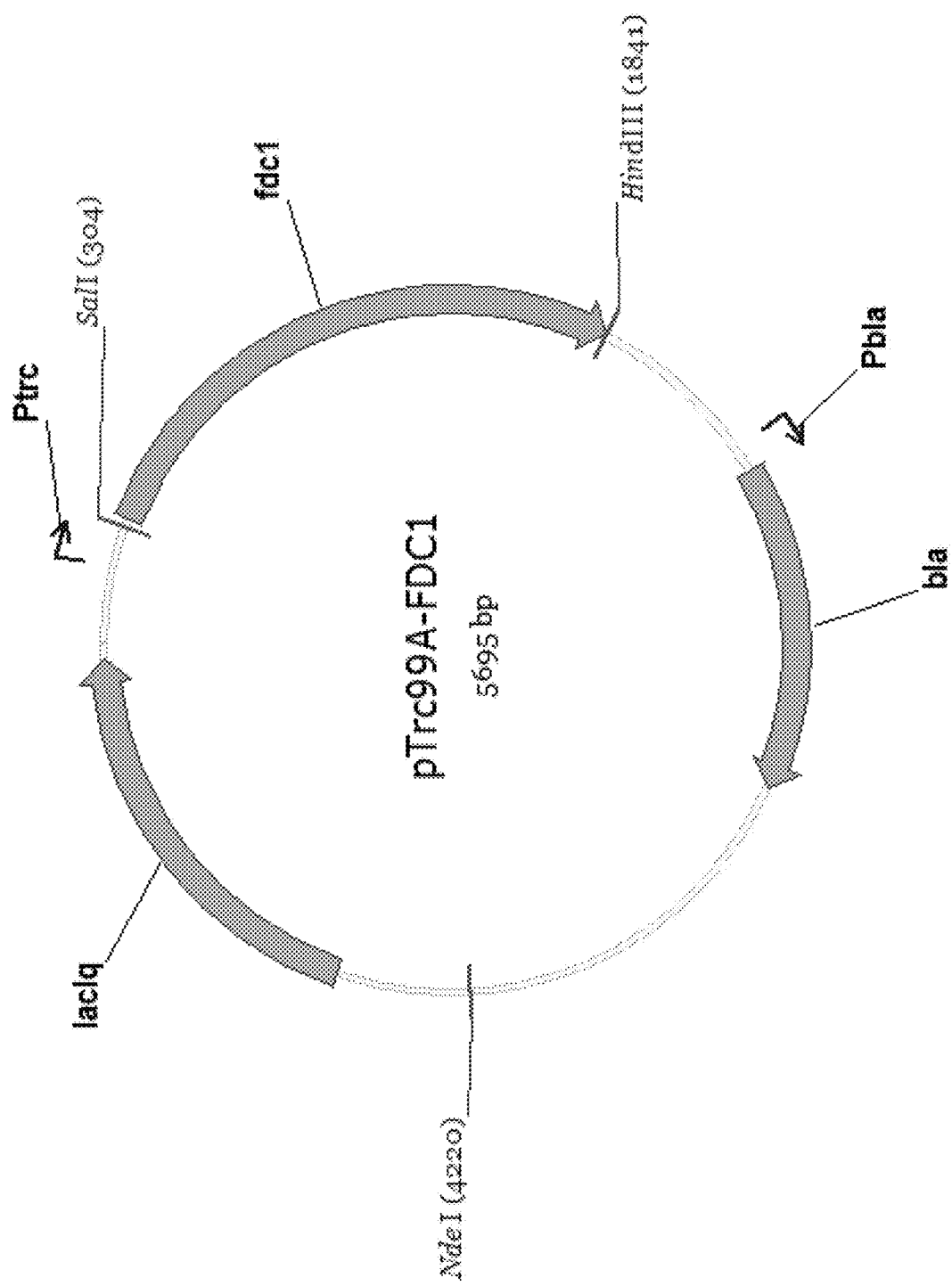
FIG. 2 illustrates a map of recombinant plasmid pTrc99A-FDC1, according to an embodiment.

PCR reactions were performed using a BioRad iCycler system with Phusion DNA Polymerase (Finnzymes, Espoo, Finland). Custom DNA oligonucleotide primers were synthesized from and purchased from Integrated DNA Technologies (Coralville, Iowa). PCR cycling and reaction conditions were standardized according to manufacturer instructions. SEQ ID NO:1, a candidate 2,4-pentadienoate decarboxylase encoding gene, was amplified via PCR using genomic DNA from *S. cerevisiae* as template. The oligonucleotides primers used to amplify FDC1 from *S. cerevisiae* (SEQ ID NO:1) are given as SEQ ID NO:3, and SEQ ID NO:4. In all cases, amplified DNA fragments were subsequently cleaned using Zyppy Clean and Concentrator kit (Zymo Research, Orange, Calif.). Fragments were then treated by restriction enzyme digestion with appropriate enzymes and buffer for 3 h at 37° C. The amplified DNA fragment containing FDC1 was digested with SalI and HindIII for which the *E. coli* expression vector pTrc99A [2] (SEQ ID NO:2; GenBank: U13872.1) was also digested with SalI and HindIII for the insertion of FDC1. All digested fragments were subsequently purified using the Zyppy Gel DNA recovery kit (Zymo Research, Orange, Calif.) per manufacturers instruction. Gene inserts and linearized plasmid DNA were then appropriately ligated together by treatment with T4 DNA ligase (New England Biolabs, Ipswich, Mass.) at 4° C. overnight. Ligase reaction mixtures were then transformed into chemically competent *E. coli* NEB10-Beta. Selection of transformants was achieved by plating transformed cells on LB solid agar media containing 100 mg/L ampicillin and culturing overnight at 37° C. The vector with the correct gene insert for FDC1 was confirmed among clones by digestion with restriction enzymes HindIII and NdeI. Under these conditions, vectors containing the correct gene insert were identified as those which displayed fragments of 3.3 kb and 2.4 kb when separated on a 0.7% w./v. agarose gel at 90V for 60 min. These cloning works resulted in the successful generation of the plasmid pTrc99A-FDC1 (shown in FIG. 2).

Example 1

Figure 3:
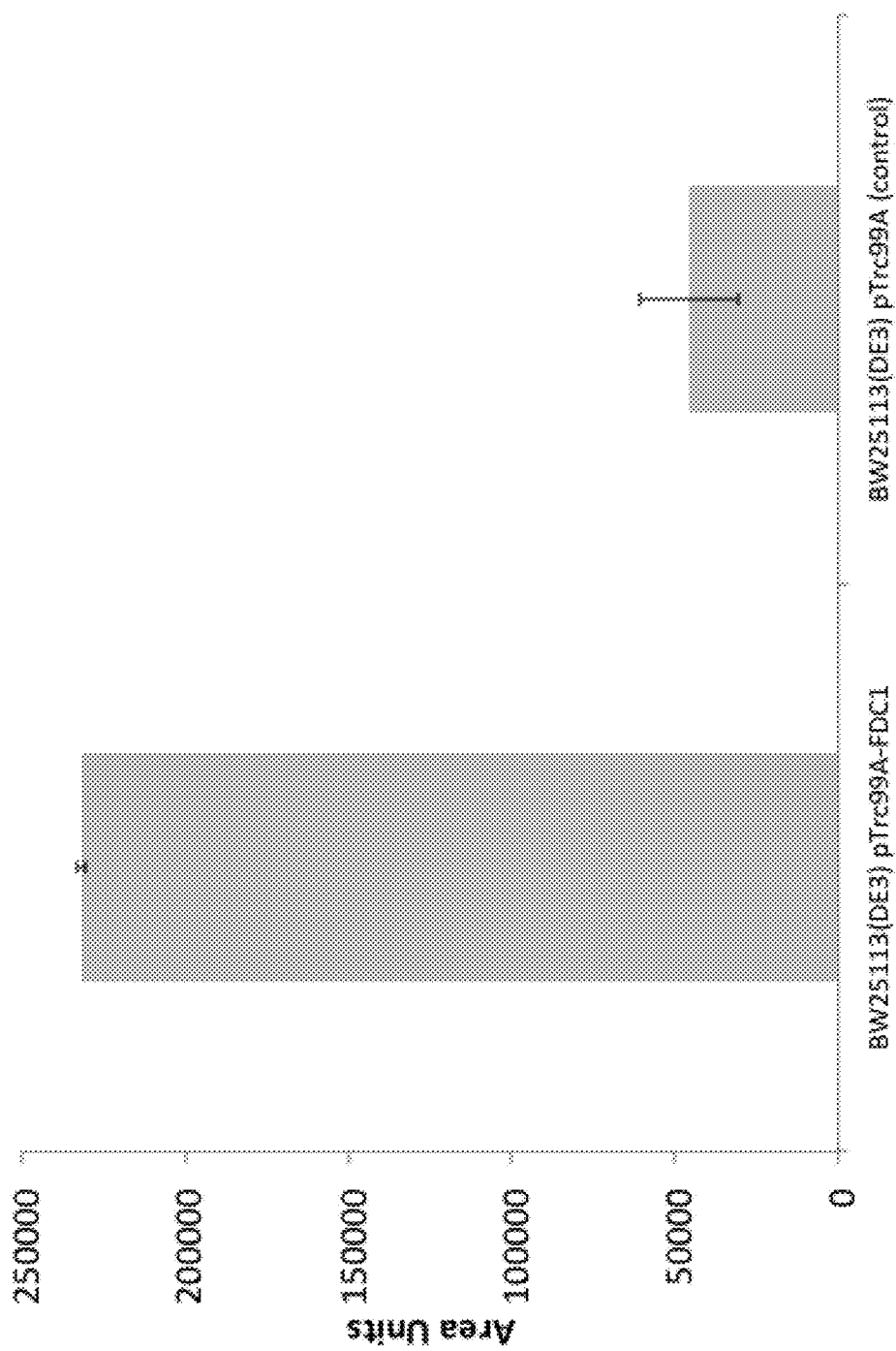
FIG. 3 demonstrates accumulation of 1,3-butadiene in the headspace of resting cell cultures of *E. coli* BW25113(DE3) pTrc99A-FDC1 and *E. coli* BW25113(DE3) pTrc99A incubated in the presence of trans-2,4-pentadienoate, as measured by GC-FID and represented in 'Area Units', according to an embodiment.
Figure 4:
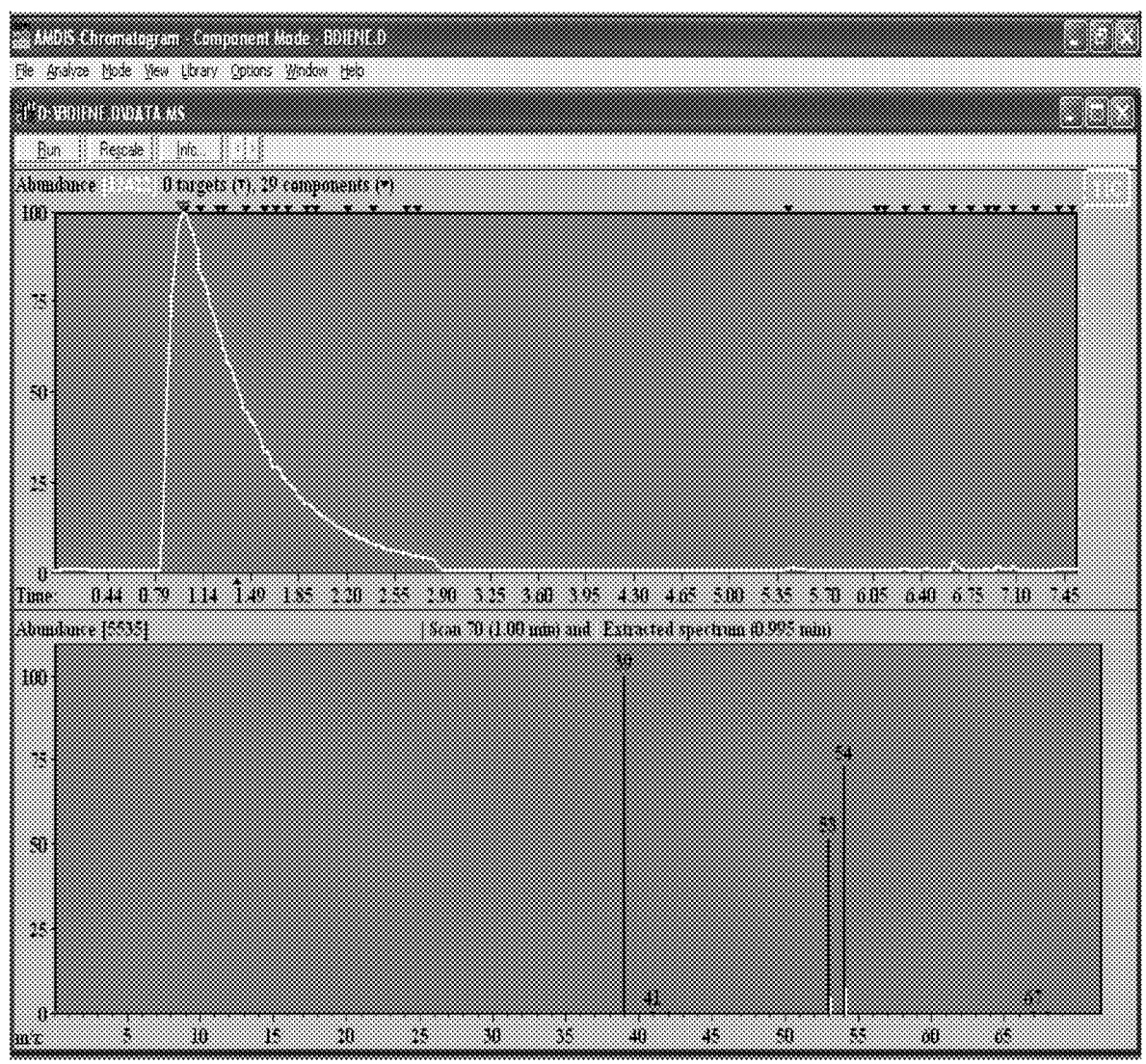
FIG. 4 compares the mass spectrum of the predominant peak obtained in the headspace over cultures of *E. coli* BW25113(DE3) pTrc99A-FDC1 incubated in minimal media supplemented with trans-2,4-pentadienoate with that of a known library reference for 1,3-butadiene.
Figure 4:
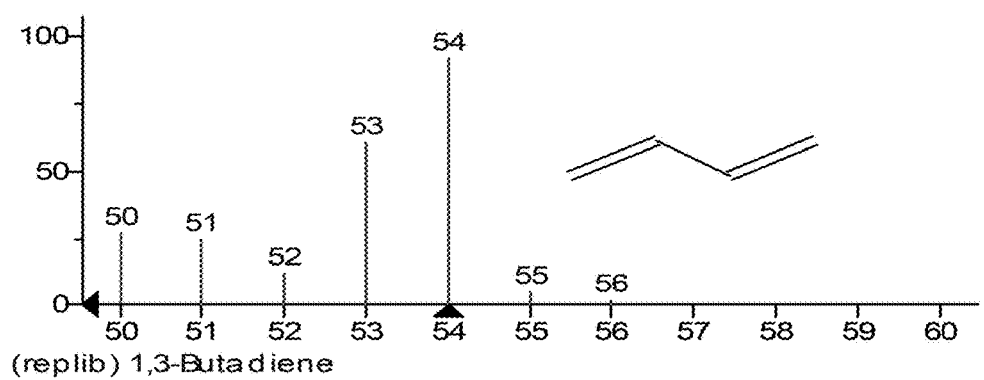

Assaying trans-2,4-pentadienoate Decarboxylase Activity in Recombinant *E. Coli* by gc-fid and gc-ms trans-2,4-Pentadienoate decarboxylase activity was investigated using a whole cell assay. *E. coli* BW25113(DE3) was first transformed with pTrc99A-FDC1. *E. coli* BW25113 (DE3) was also similarly transformed with pTrc99A as control. Selection was performed on LB agar supplemented with 100 mg/L ampicillin and screened for said resistance. This resulted in the construction of the *E. coli* strains BW25113(DE3) pTrc99A-FDC1 and BW25113(DE3) pTrc99A. Seed cultures of both strains consisting of 5 ml of LB broth containing 100 mg/L ampicillin were each prepared and grown overnight at 37° C. while shaking at 200 rpm. 1 mL of each culture was used to inoculate 3×250 mL shake flasks containing 50 mL of LB supplemented with 100 mg/L. Cultures were grown at 37° C. while shaking at 200 rpm for 6 h before being induced with IPTG to a final concentration of 0.25 mM. Induced cultures were then allowed to grow overnight at 37° C. while shaking at 200 rpm. Cells were then collected by centrifugation in 50 ml Falcon tubes for 5 min at 3000×g and washed once with PBS (phosphate buffered saline, pH 7) buffer. The entire cell pellet was then resuspended in 30 ml PBS supplemented with 500 mg/L of trans-2,4-pentadienoate and transferred to glass anaerobic culture tubes sealed with an aluminum lined rubber cap. After 12 hours of shaking at 200 rpm and 37° C., gas samples were taken directly from the headspace of the glass vials by puncturing the aluminum lined rubber cap with a Hamilton gas tight syringe (Reno, Nev.). Samples were injected directly onto both a gas chromatograph coupled with a flame ionization detector (FID) and a gas chromatograph coupled with a Mass Spectroscopy (MS) detector. In both cases separation was achieved using an Agilent DB-5 GC column. As shown in FIG. 3, the production of 1,3-butadiene was confirmed with FID by detection of its accumulation in the headspace above cultures of BW25113(DE3) pTrc99A-FDC1 to levels at least 5-fold greater than in the headspace above the BW25113(DE3) pTrc99A control cultures. Further support of trans-2,4-pentadienoate decarboxylase activity was provided from GC-MS analysis of culture headspaces (FIG. 4). The approximate molecular weight of 1,3-butadiene is 54. GC-MS analysis of headspaces above cultures supplied with trans-2,4-pentadienoate revealed a peak with the highest relative abundance at the mass-to-charge ratio (m/z) of 54. This additional analysis provided definitive evidence of the production and accumulation 1,3-butadiene.

These results demonstrate how trans-2,4-pentadienoate decarboxylase activity can be attained in recombinant *E. coli* by the expression of a gene whose sequence is given by SEQ ID NO:1. These results further establish the generation of a recombinant *E. coli* strain that is specifically capable of converting trans-2,4-pentadienoate to 1,3-butadiene.

Example 2

Assaying trans-2,4-pentadienoate Decarboxylase Activity in Recombinant *E. Coli* by FIS

*E. coli* BL21(DE3) was first transformed with pTrc99A-FDC1. *E. coli* BL21(DE3) was also similarly transformed with pTrc99A as control. Selection was performed on LB agar supplemented with 100 mg/L ampicillin and screened for said resistance. This resulted in the construction of the *E. coli* strains BL21(DE3) pTrc99A-FDC1 and BL21(DE3) pTrc99A. Cells were grown from two different colonies for each strain in LB media with 100 mg/L ampicillin at 32° C. overnight while shaking at 250 rpm. From these seed cultures, 200 μL were then inoculated into 10 mL fresh LB media supplemented with appropriate antibiotics and grown until reaching an $OD_{600}$ of about 0.6. Then, cultures were induced by adding 0.2 mM IPTG before being cultured for an additional 6 hours at 32° C. while shaking at 250 rpm. Next, 8 mL of each culture was collected and pelleted by centrifugation. Cells were then washed with PBS buffer and finally resuspended in 3 ml of fresh PBS buffer. These samples were then used for two different sets of experiments. In the first, 1 ml of washed cells were transferred to the gas vials and trans-2,4-pentadienoate was added to final concentration 1 mg/ml. In the second, 1 ml of washed cells were added to LB media supplemented with appropriate antibiotics and trans-2,4-pentadienoate at a final concentration 1 mg/ml. All samples were incubated at 32° C. while shaking at 250 rpm. After both 3 hours and 24 hours, samples of the culture headspace were removed for analysis in triplicate by FIS (Hills-Scientific) at the inlet line and reaction cell at 70° C. The FIS readout was calibrated with 1,3-butadiene standards. The results for both experiments are shown in Tables 1 and 2.

These results further demonstrate how trans-2,4-pentadienoate decarboxylase activity can be attained in recombinant *E. coli* by the expression of a gene whose sequence is given by SEQ ID NO:1. These results further establish the generation of recombinant *E. coli* strains that are specifically capable of converting trans-2,4-pentadienoate to 1,3-butadiene.

Example 3

Assaying cis-2,4-pentadienoate Decarboxylase Activity in Recombinant *E. Coli* by FIS

*E. coli* BL21(DE3) was first transformed with pTrc99A-FDC1. *E. coli* BL21(DE3) was also similarly transformed with pTrc99A as control. Selection was performed on LB agar supplemented with 100 mg/L ampicillin and screened for said resistance. This resulted in the construction of the *E. coli* strains BL21(DE3) pTrc99A-FDC1 and BL21(DE3) pTrc99A. Cells were grown from two different colonies for each strain in LB media with 100 mg/L ampicillin at 32° C. overnight while shaking at 250 rpm. From these seed cultures, 200 □L were then inoculated into 10 mL fresh LB media supplemented with appropriate antibiotics and grown until reaching an $OD_{600}$ of about 0.6. Then, cultures were induced by adding 0.2 mM IPTG before being cultured for an additional 6 hours at 32° C. while shaking at 250 rpm. Next, 10 mL of each culture was collected and pelleted by centrifugation. Cells were then washed with PBS buffer and finally resuspended in 2 ml of fresh PBS buffer. Next, 1 ml of washed cells were transferred to the gas vials and cis-2,4-pentadienoate was added to final concentration 1 mg/ml. All samples were incubated at 32° C. while shaking at 250 rpm. After both 3 hours and 24 hours, samples of the culture headspace were removed for analysis in triplicate by FIS at the inlet line and reaction cell at 70° C. The results are shown in Table 3.

These results further demonstrate how cis-2,4-pentadienoate decarboxylase activity can be attained in recombinant *E. coli* by the expression of a gene whose sequence is given by SEQ ID NO:1. These results further establish the generation of recombinant *E. coli* strains that are specifically capable of converting cis-2,4-pentadienoate to 1,3-butadiene.

The materials and methods described above are not intended to be limited to the embodiments and examples described herein.

What is claimed is:

1. A method for the production of 1,3-butadiene from a recombinant cell comprising:
culturing a recombinant host cell with 2,4-pentadienoate, the recombinant host cell expressing a gene comprising SEQ ID NO: 1 encoding a polypeptide having 2,4-pentadienoate decarboxylase activity, wherein expression in the recombinant host cell of the gene comprising SEQ ID NO: 1 encoding the polypeptide having 2,4-pentadienoate decarboxylase activity provides increased production of 1,3-butadiene in the recombinant host cell relative to a control recombinant host cell lacking expression of the gene comprising SEQ ID NO: 1 encoding the polypeptide having 2,4-pentadienoate decarboxylase activity.

2. The method according to claim 1 wherein the polypeptide having 2,4-pentadienoate decarboxylase activity has trans-2,4-pentadienoate decarboxylase activity.

3. The method according to claim 1 wherein the polypeptide having 2,4-pentadienoate decarboxylase activity has cis-2,4-pentadienoate decarboxylase activity.

4. The method according to claim 1 wherein the gene comprising SEQ ID NO: 1 encoding the polypeptide having 2,4-pentadienoate decarboxylase activity is derived from *Saccharomyces cerevisiae*.

5. The method according to claim 1 wherein the gene comprising SEQ ID NO: 1 encoding the polypeptide having 2,4-pentadienoate decarboxylase activity comprises fdc1 gene from *Saccharomyces cerevisiae*.

6. The method according to claim 1 wherein the gene comprising SEQ ID NO: 1 encoding the polypeptide having 2,4-pentadienoate decarboxylase activity is derived from an organism that comprises at least one member selected from the group consisting of bacteria, yeast, filamentous fungi, cyanobacteria, algae, and plant cells.

7. The method according to claim 1 wherein the gene comprising SEQ ID NO: 1 encoding the polypeptide having 2,4-pentadienoate decarboxylase activity is derived from an organism that comprises at least one member selected from the group consisting of *Escherichia, Salmonella, Bacillus, Acinetobacter, Streptomyces, Corynebacterium, Methylosinus, Methylomonas, Rhodococcus, Pseudomonas, Rhodobacter, Synechocystis, Saccharomyces, Klebsiella, Zygosaccharomyces, Kluyveromyces, Candida, Hansenula, Debaryomyces, Mucor, Pichia, Torulopsis, Aspergillus, Arthrobotrys, Brevibacterium, Microbacterium, Arthrobacter, Citrobacter, Chlamydomonas, Fusarium, Penicillium*, and *Zymomonas*.

8. The method according to claim 1 wherein the recombinant host cell comprises at least one member selected from the group consisting of bacteria, yeast, filamentous fungi, cyanobacteria, algae, and plant cells.

9. The method according to claim 1 wherein the recombinant host cell comprises at least one member selected from the group consisting of *Escherichia, Salmonella, Bacillus, Acinetobacter, Streptomyces, Corynebacterium, Methylosinus, Methylomonas, Rhodococcus, Pseudomonas, Rhodobacter, Synechocystis, Saccharomyces, Klebsiella, Zygosaccharomyces, Kluyveromyces, Candida, Hansenula, Debaryomyces, Mucor, Pichia, Torulopsis, Aspergillus, Arthrobotrys, Brevibacterium, Microbacterium, Arthrobacter, Citrobacter, Chlamydomonas, Fusarium, Penicillium*, and *Zymomonas*.

* * * * *

SEQUENCE LISTING

<160> NUMBER OF SEQ ID NOS: 4

<210> SEQ ID NO 1
<211> LENGTH: 1512
<212> TYPE: DNA
<213> ORGANISM: SACCHAROMYCES CEREVISIAE

<400> SEQUENCE: 1

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga agtaagga gaaggagat       240 catggtagaa ttgcccatca tctggggctc gacccaaaaa caactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct tgggtgagtc ggttccagta gtaaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
```

-continued

| | |
|---|---|
| gaattttgta agaaggtagg tgatatttac tttaggacaa agttggtttt tatagtccat | 1200 |
| gaaataattt tggtggcaga tgatatcgac atatttaact tcaaagaagt catctgggcc | 1260 |
| tacgttacaa gacatacacc tgttgcagat cagatggctt ttgatgatgt cacttctttt | 1320 |
| cctttggctc cctttgtttc gcagtcatcc agaagtaaga ctatgaaagg tggaaagtgc | 1380 |
| gttactaatt gcatatttag acagcaatat gagcgcagtt ttgactacat aacttgtaat | 1440 |
| tttgaaaagg gatatccaaa aggattagtt gacaaagtaa atgaaaattg gaaaaggtac | 1500 |
| ggatataaat aa | 1512 |

<210> SEQ ID NO 2
<211> LENGTH: 4176
<212> TYPE: DNA
<213> ORGANISM: E. COLI

<400> SEQUENCE: 2

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg caaatattc | 180 |
| tgaaatgagc tgttgacaat taatcatccg gctcgtataa tgtgtggaat tgtgagcgga | 240 |
| taacaatttc acacaggaaa cagaccatgg aattcgagct cggtacccgg ggatcctcta | 300 |
| gagtcgacct gcaggcatgc aagcttggct gttttggcgg atgagagaag attttcagcc | 360 |
| tgatacagat taaatcagaa cgcagaagcg gtctgataaa acagaatttg cctggcggca | 420 |
| gtagcgcggt ggtcccacct gaccccatgc cgaactcaga agtgaaacgc cgtagcgccg | 480 |
| atggtagtgt ggggtctccc catgcgagag tagggaactg ccaggcatca ataaaacga | 540 |
| aaggctcagt cgaaagactg ggcctttcgt tttatctgtt gtttgtcggt gaacgctctc | 600 |
| ctgagtagga caaatccgcc gggagcggat ttgaacgttg cgaagcaacg gcccggaggg | 660 |
| tggcgggcag gacgcccgcc ataaactgcc aggcatcaaa ttaagcagaa ggccatcctg | 720 |
| acggatggcc ttttttgcgtt tctacaaact cttttttgttt atttttctaa atacattcaa | 780 |
| atatgtatcc gctcatgaga caataaccct gataaatgct tcaataatat tgaaaaagga | 840 |
| agagtatgag tattcaacat ttccgtgtcg cccttattcc cttttttgcg cattttgcc | 900 |
| ttcctgtttt tgctcaccca gaaacgctgg tgaaagtaaa agatgctgaa gatcagttgg | 960 |
| gtgcacgagt gggttacatc gaactggatc tcaacagcgg taagatcctt gagagttttc | 1020 |
| gccccgaaga acgttttcca atgatgagca cttttaaagt tctgctatgt ggcgcggtat | 1080 |
| tatcccgtgt tgacgccggg caagagcaac tcggtcgccg catacactat tctcagaatg | 1140 |
| acttggttga gtactcacca gtcacagaaa agcatcttac ggatggcatg acagtaagag | 1200 |
| aattatgcag tgctgccata accatgagtg ataacactgc ggccaactta cttctgacaa | 1260 |
| cgatcggagg accgaaggag ctaaccgctt ttttgcacaa catgggggat catgtaactc | 1320 |
| gccttgatcg ttgggaaccg gagctgaatg aagccatacc aaacgacgag cgtgacacca | 1380 |
| cgatgcctac agcaatggca acaacgttgc gcaaactatt aactggcgaa ctacttactc | 1440 |
| tagcttcccg gcaacaatta atagactgga tggaggcgga taaagttgca ggaccacttc | 1500 |
| tgcgctcggc ccttccggct ggctggttta ttgctgataa atctggagcc ggtgagcgtg | 1560 |
| ggtctcgcgg tatcattgca gcactggggc cagatggtaa gccctcccgt atcgtagtta | 1620 |
| tctacacgac ggggagtcag gcaactatgg atgaacgaaa tagacagatc gctgagatag | 1680 |
| gtgcctcact gattaagcat tggtaactgt cagaccaagt ttactcatat atactttaga | 1740 |

```
ttgatttaaa acttcattttt taatttaaaa ggatctaggt gaagatcctt tttgataatc    1800
tcatgaccaa aatcccttaa cgtgagtttt cgttccactg agcgtcagac cccgtagaaa    1860
agatcaaagg atcttcttga gatccttttt ttctgcgcgt aatctgctgc ttgcaaacaa    1920
aaaaaccacc gctaccagcg gtggtttgtt tgccggatca agagctacca actctttttc    1980
cgaaggtaac tggcttcagc agagcgcaga taccaaatac tgtccttcta gtgtagccgt    2040
agttaggcca ccacttcaag aactctgtag caccgcctac atacctcgct ctgctaatcc    2100
tgttaccagt ggctgctgcc agtggcgata gtcgtgtct taccgggttg gactcaagac    2160
gatagttacc ggataaggcg cagcggtcgg gctgaacggg gggttcgtgc acacagccca    2220
gcttggagcg aacgacctac accgaactga gatacctaca gcgtgagcta tgagaaagcg    2280
ccacgcttcc cgaagggaga aaggcggaca ggtatccggt aagcggcagg gtcggaacag    2340
gagagcgcac gagggagctt ccaggggaa acgcctggta tctttatagt cctgtcgggt    2400
ttcgccacct ctgacttgag cgtcgatttt tgtgatgctc gtcaggggg cggagcctat    2460 ggaaaaacgc cagcaacgcg gccttttac ggttcctggc cttttgctgg ccttttgctc    2520
acatgttctt tcctgcgtta tcccctgatt ctgtggataa ccgtattacc gcctttgagt    2580
gagctgatac cgctcgccgc agccgaacga ccgagcgcag cgagtcagtg agcgaggaag    2640
cggaagagcg cctgatgcgg tattttctcc ttacgcatct gtgcggtatt tcacaccgca    2700
tatggtgcac tctcagtaca atctgctctg atgccgcata gttaagccag tatacactcc    2760
gctatcgcta cgtgactggg tcatggctgc gccccgacac ccgccaacac ccgctgacgc    2820
gccctgacgg gcttgtctgc tcccggcatc cgcttacaga caagctgtga ccgtctccgg    2880
gagctgcatg tgtcagaggt tttcaccgtc atcaccgaaa cgcgcgaggc agcagatcaa    2940
ttcgcgcgcg aaggcgaagc ggcatgcatt tacgttgaca ccatcgaatg gtgcaaaacc    3000
tttcgcggta tggcatgata gcgcccggaa gagagtcaat tcagggtggt gaatgtgaaa    3060
ccagtaacgt tatacgatgt cgcagagtat gccggtgtct cttatcagac cgtttcccgc    3120
gtggtgaacc aggccagcca cgtttctgcg aaaacgcggg aaaaagtgga agcggcgatg    3180
gcggagctga attacattcc caaccgcgtg gcacaacaac tggcgggcaa acagtcgttg    3240
ctgattggcg ttgccacctc cagtctggcc ctgcacgcgc cgtcgcaaat tgtcgcggcg    3300
attaaatctc gcgccgatca actgggtgcc agcgtggtgg tgtcgatggt agaacgaagc    3360
ggcgtcgaag cctgtaaagc ggcggtgcac aatcttctcg cgcaacgcgt cagtgggctg    3420
atcattaact atccgctgga tgaccaggat gccattgctg tggaagctgc ctgcactaat    3480
gttccggcgt tatttcttga tgtctctgac cagacaccca tcaacagtat tattttctcc    3540
catgaagacg gtacgcgact gggcgtggag catctggtcg cattgggtca ccagcaaatc    3600
gcgctgttag cgggcccatt aagttctgtc tcggcgcgtc tgcgtctggc tggctggcat    3660
aaatatctca ctcgcaatca aattcagccg atagcggaac gggaaggcga ctggagtgcc    3720
atgtccggtt ttcaacaaac catgcaaatg ctgaatgagg gcatcgttcc cactgcgatg    3780
ctggttgcca acgatcagat ggcgctgggc gcaatgcgcg ccattaccga gtccgggctg    3840
cgcgttggtg cggatatctc ggtagtggga tacgacgata ccgaagacag ctcatgttat    3900
atcccgccgt caaccaccat caaacaggat tttcgcctgc tggggcaaac cagcgtggac    3960
cgcttgctgc aactctctca gggccaggcg gtgaagggca atcagctgtt gcccgtctca    4020
ctggtgaaaa gaaaaaccac cctggcgccc aatacgcaaa ccgcctctcc ccgcgcgttg    4080
```

```
gccgattcat taatgcagct ggcacgacag gtttcccgac tggaaagcgg gcagtgagcg    4140
caacgcaatt aatgtgagtt agcgcgaatt gatctg                              4176

<210> SEQ ID NO 3
<211> LENGTH: 49
<212> TYPE: DNA
<213> ORGANISM: Artificial Sequence
<220> FEATURE:
<223> OTHER INFORMATION: synthetic

<400> SEQUENCE: 3
atagtcgaca gacatcaaag gacggttcat gaggaagcta aatccagct               49

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
attaagcttt tatttatatc cgtacctttt ccaat                              35
```